United States Patent [19]

Schmatz

[11] Patent Number: 5,089,478
[45] Date of Patent: Feb. 18, 1992

[54] METHOD FOR THE CONTROL OF PNEUMOCYSTIS CARINII

[75] Inventor: Dennis M. Schmatz, Cranford, N.J.

[73] Assignee: Merck & Co., Inc., Rahway, N.J.

[21] Appl. No.: 259,019

[22] Filed: Oct. 17, 1988

[51] Int. Cl.$^5$ .............................................. A61K 31/70
[52] U.S. Cl. .................................... 514/25; 536/16.8; 536/18.1
[58] Field of Search ................. 514/25; 536/16.8, 18.1

[56] References Cited

U.S. PATENT DOCUMENTS

| 4,278,665 | 7/1981 | Traxler | 514/25 |
| 4,374,129 | 2/1983 | Traxler | 514/25 |

OTHER PUBLICATIONS

P. Traxler et al., J. Antibiotics XXX (4) 289 (1977).
P. Traxler et al., J. Antibiotics XXXIII (9) 967 (1980).
G. Rommele et al., J. Antibiotics XXXVI (II) 1539 (1983).
P. Traxler et al., J. Antibiotics XL (8) 1146 (1987).
CRC Handbook of Antibiotic Compounds, vol. 1, CRC Press, Inc., Boca Raton, FL—pp. 396–397.
T. Komori et al., J. Antibiotics XXXVIII (4) 544 (1985).
T. Komori et al., J. Antibiotics XXXVIIII (4) 455 (1985).

*Primary Examiner*—Johnnie R. Brown
*Assistant Examiner*—Elli Peselev
*Attorney, Agent, or Firm*—Alice O. Robertson; Hesna J. Pfeiffer

[57] ABSTRACT

There is disclosed a new method for the treatment of *Pneumocystis carinii*, the causative agent of pneumonia of particular severity to immune-compromised patients such as those with acquired immune deficiency syndrome (AIDS). The method concerns the administration of a papulacandin compound.

5 Claims, No Drawings

METHOD FOR THE CONTROL OF PNEUMOCYSTIS CARINII

BACKGROUND OF THE INVENTION

*Pneumocystis carinii* is an opportunistic organism, widely prevalent but generally dormant until bodily defenses are compromised whereupon it attacks the host. Generally, it is present in the lungs, thus pneumonia, frequently fatal, is the consequence of an infective attack. Also, patient to patient transmission can occur between similarly immune-compromised patients. The loss of immunity is associated with defects in the cell mediated immunity as is the case with patients with hematologic immunosuppression deficiencies, patients with lymphoproliferative diseases, patients under cancer chemotherapy, and patients with AIDS or with immunosuppressed transplants. About one half of the AIDS patients develop *P. carinii* pneumonia and AIDS patients have accounted for most of the recent cases of this disease. Left untreated, the disease is 100 percent fatal.

The current method of treatment for *P. carinii* pneumonia is trimethoprim/sulfamethoxazole or pentamidine. Treatment with trimethoprim/sulfamethoxazole (TMP/SMZ) is associated with a high level of toxic side effects including rash, elevated liver function, nausea and vomiting, anemia, creatine elevation, and in extreme cases, Stevens Johnson syndrome. Side effects from TMP/SMZ are much more prevalent in patients with AIDS. Treatment with pentamidine is also associated with a high level of toxic side effects including renal failure, hepatotoxicity, hypoglycemia, hematologic abnormalities and pain or abscess at the injection site. The mortality attributable to treatment can reach 20 to 30 percent. An improved method for the treatment of *P. carinii* pneumonia in immune compromised patients is greatly needed.

STATEMENT OF THE INVENTION

The present invention is concerned with the treatment of or the prevention of *Pneumocystis carinii* in mammals by administering a papulacandin compound.

DESCRIPTION OF THE INVENTION

The present invention comprises administering to a mammalian host infected with or susceptible to becoming infected with *Pneumocystis carinii* a therapeutic or anti infective amount of a papulacandin compound or a mixture thereof. By "papulacandin compound" is meant (1) secondary metabolites obtained by the cultivation of the microorganism *Papularia sphaerosperma*, especially of the strain NRRL 8086, hereinafter referred to as the papulacandin antibiotics and (2) derivatives of (1) consisting of
  (a) ethers of (1)
  (b) esters of (1)
  (c) hydrogenation products of (1)
  (d) ethers of (2)(c)
  (e) esters of (2)(c)
  (f) N-acyl 11-amino derivatives of (1).

The papulacandin antibiotics and ethers and esters thereof may be represented by the following formula:

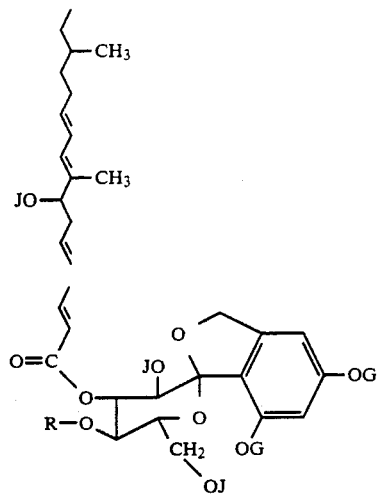

wherein R may be

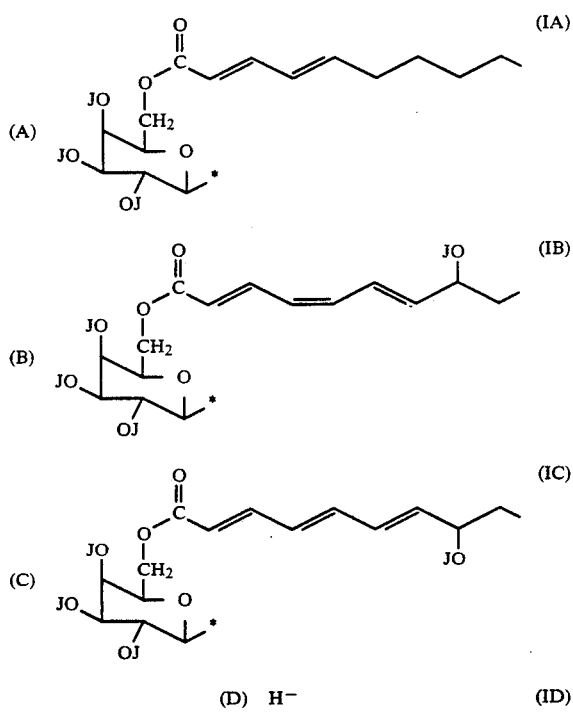

wherein * is the point of bonding, G is hydrogen or lower alkyl and J is hydrogen or acyl containing from 1 to 20 carbon atoms provided that at least one of J and G is hydrogen.

In the foregoing formulas, when G and J are hydrogen, formula (IA) is the formula for the antibiotic known in the literature as Papulacandin A, (IB) for Papulacandin B, (IC) for Papulacandin C and (ID) for Papulacandin D. In addition, there is papulacandin E in the natural antibiotics, the structure of which is not reported.

The hydrogenation products of the secondary metabolites may be represented by formula (II) wherein:
  G is hydrogen or lower alkyl; and
  J is hydrogen or lower alkyl.

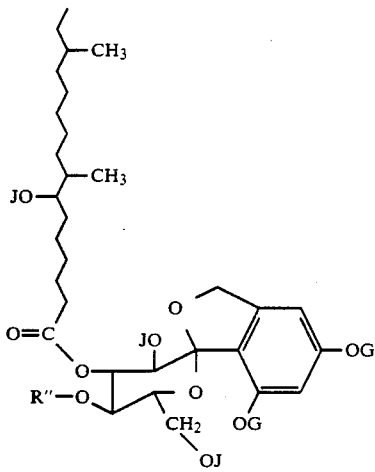

wherein R″ may be

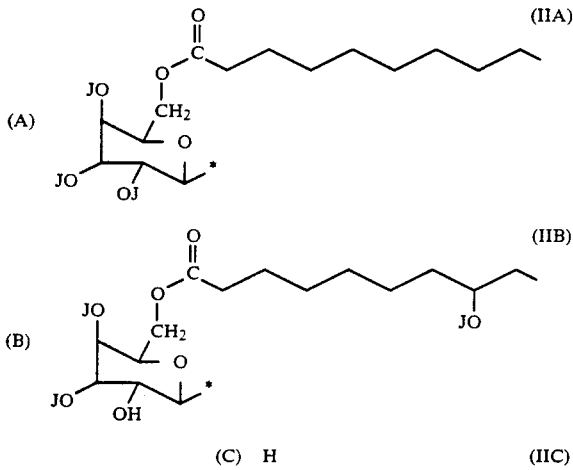

and wherein * is the point of bonding, G and J are as previously defined and wherein at least one of G and J must be hydrogen.

These secondary metabolites and their production, isolation and identification may be found in U.S. Pat. No. 4,278,665, and Journal of Antibiotics, XXX (4), 289 (1977) and XXXIII (9) 967 (1980). The preparation of the ethers and esters of the papulacandin antibiotics, and the preparation of the hydrogenation product and their esters and ethers are described in the foregoing U.S. Pat. No. 4,278,665 and the teachings of the foregoing patent and articles are incorporated by reference.

The N-acyl 11-amino derivatives of papulacandin A or B which are also within the scope of the present invention may be represented by the formula (III)

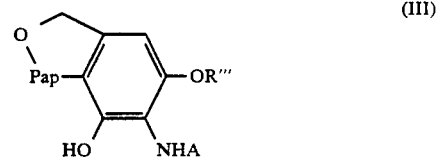

wherein R′″ represents hydrogen or methyl, and A represents hydrogen or an acyl radical of an α-amino acid which occurs naturally as a peptide building unit, or of a lower alkanesulfonic acid having a maximum of 7 carbon atoms, or of a lower alkanoic acid having a maximum of 7 carbon atoms, or the acyl radical of the formula

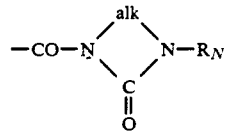

in which $R_N$ represents hydrogen, formyl, lower alkoxycarbonyl, carbamoyl, hydroxy-lower alkyl or a hydrocarbyl having a maximum of 8 carbon atoms, and "alk" represents an alkylene radical having from 2 to 8 carbon atoms and which separates the two nitrogen atoms from each other by a minimum of 2 and a maximum of 4 carbon atoms; or an acid addition salt of said compound when the acyl radical is an α-amino acid.

The preferred compounds are the papulacandin antibiotics represented by the following formulas:

(A) Papulacandin A having the formula

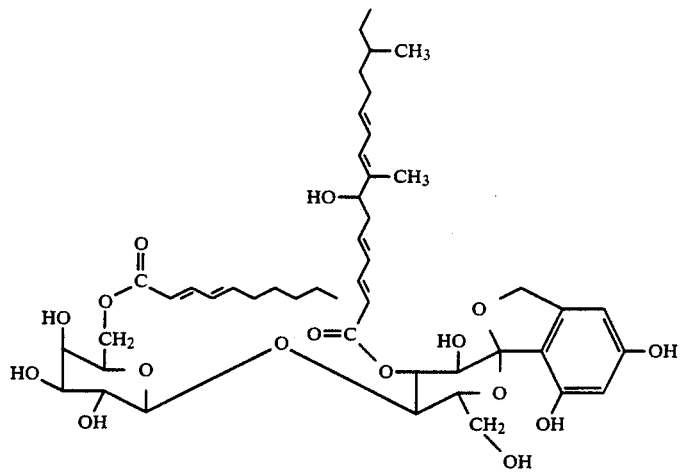

and having Chemical Abstracts name of alpha-D-glucopyranose, 1,16-anhydro-1-C-[2,4-dihydroxy-6-(hydroxy-methyl)phenyl]-4-0-[6-0-(1-oxo-2,4- decadienyl)-beta-D-galactopyranosyl]-, 3-(7-hydroxy-8,14-dimethyl-2,4,8,10-hexadecatetraenoate)

(B) Papulacandin B having the formula

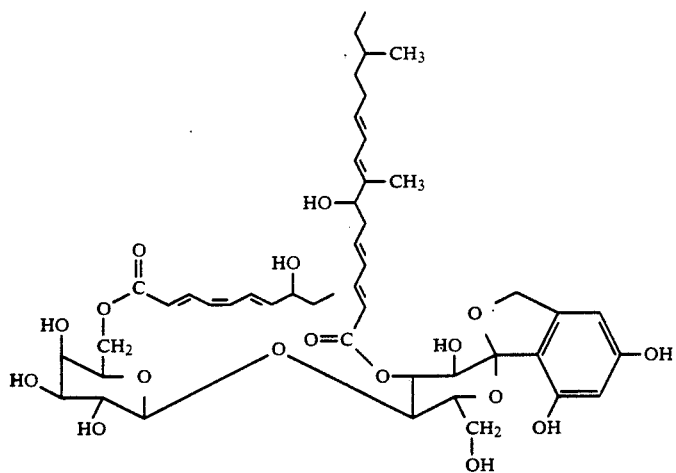

and having the Chemical Abstracts name of alpha-D-glucopyranose, 1,16-anhydro-1-C-[2,4-dihydroxy-6-(hydroxymethyl)phenyl]-4-0-[6-0-(1-oxo-2,4-decadienyl)-beta-D-galactopyranosyl]-, 3-(7-hydroxy-8,14-dimethyl-2,4,8,10-hexadecatetraenoate).

(C) Papulacandin C having the formula

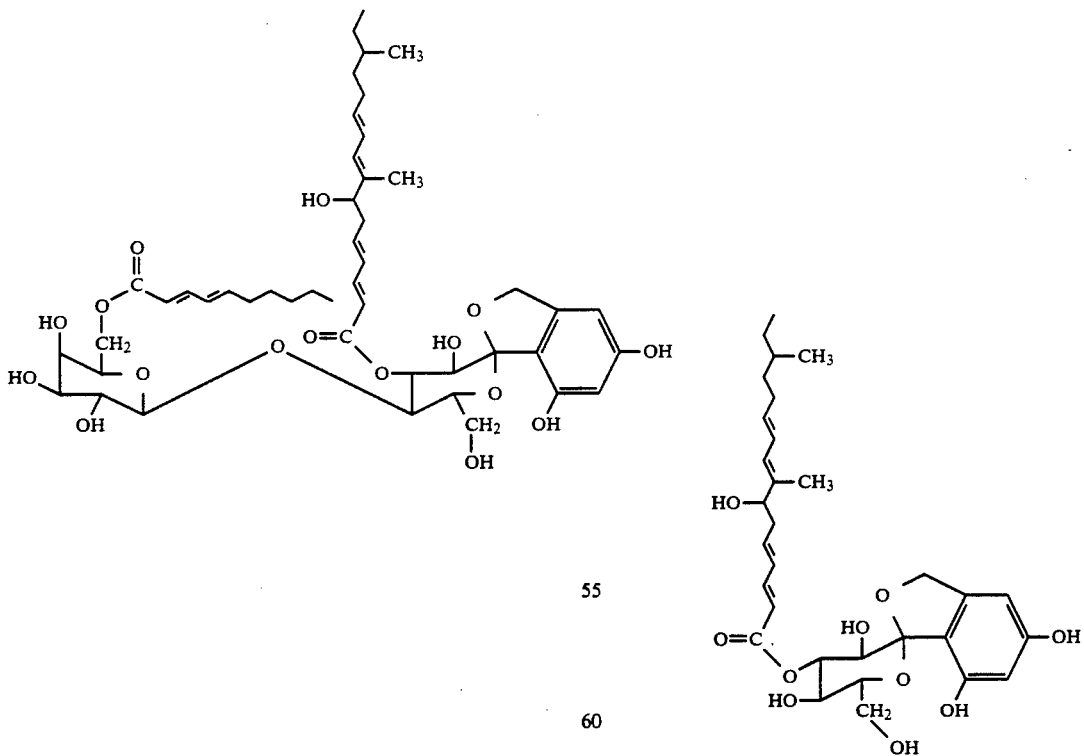

and having the Chemical Abstracts name of alpha-D-glucopyranose, 1,16-anhydro-1-C-[2,4-dihydroxy-6-(hydroxymethyl)phenyl]-4-0-[6-0-(1-oxo-2,4-decadienyl)-beta-D-galactopyranosyl]-, 3-(7-hydroxy-8,14-dimethyl-2,4,8,10-hexadecatetraenoate)

(D) Papulacandin D having the formula and having the Chemical Abstracts name of alpha-D-glucopyranose, 1,16-anhydro-1-C-[2,4-dihydroxy-6-(hydroxymethyl)phenyl]-4-0-[6-0-(1-oxo-2,4-decadienyl)-beta-D-galactopyranosyl]-, 3-(7-hydroxy-8,14-dimethyl-2,4,8,10-hexadecatetraenoate) and (E) Papulacandin E or mixtures thereof.

Most preferred are Papulacandin A and Papulacandin B.

The papulacandin compounds are white, crystalline or powdery substances of good solubility in lower alkanols and other polar solvents such as dimethylformamide, dimethyl sulfoxide, acetone and the like; and of poor solubility in water, hydrocarbons such as hexane or benzene, and ethers.

Some properties of the papulacandin antibiotics, as reported in U.S. Pat. No. 4,278,665, are as follows:

Papulacandin A is a white, crystalline, weakly acidic compound of the following physical properties:
m. p. 171°–173° C. (dec.)
U.V. spectrum (in ethanol).

| $\lambda_{max}$ 232 nm (shoulder) |
|---|
| 242 nm ($E_{max}$ = 425) |
| 265 nm ($E_{max}$ = 520) | optical rotation
$[\alpha]_D 20 = +30° \pm 1°$ (c=0.419 in methanol).

Papulacandin B is a white powdery, acidic compound of the following physical properties:
m.p. 193°–197° C. (dec.).
U.V. spectrum (in ethanol)

| $\lambda_{max}$ 232 nm (E = 42,000) |
|---|
| 240 nm (E = 42,400) |
| 268 nm (E = 44,800) |
| 300 nm (E = 31,200) | optical rotation
$[\alpha]_D 20 = +50.0° +1°$ (C=0.46 in methanol).

Papulacandin C is a white powdery, weakly acidic substance shown to be a stereoisomer of the physical properties:
m p. 140°–150° C. (dec.).
U.V. spectrum (in ethanol)

| $\lambda_{max}$ 232 nm |
|---|
| 240 nm |
| 268 nm |
| 297 sh | optical rotation
$[\alpha]_D 22 = +33° \pm 1°$ (in methanol).

Papulacandin D is a white powdery, weakly acidic substance compound of the following physical properties:
m.p. 127°–130° C.
U.V. spectrum (in ethanol)

| $\lambda_{max}$ 230 nm ($E_{max}$ = 340) |
|---|
| 235 nm (shoulder) |
| 261 nm ($E_{max}$ = 320) |

Papulacandin E is a white powdery, weakly acidic substance compound of the following physical properties:
U. V. spectrum (in ethanol).

| $\lambda_{max}$ 230 nm ($E_{max}$ = 270) |
|---|
| 237 nm (shoulder) |
| 267 nm ($E_{max}$ = 300) |
| 292 nm (shoulder) |

Details on the IR and NMR spectra may be found in the aforecited patent which is incorporated by reference.

The papulacandins may be produced by the cultivation of the microorganism *Papularia sphaerosperma strain A* 32283 which was deposited in the Northern Regional Research Lab., U.S. Department of Agriculture, Peoria, Ill., under No. NRRL 8086 as fully described in U.S. Pat. No. 4,278,665, which teachings are incorporated by reference.

The papulacandins are formed when the specie *papularia sphaerosperma* is cultured in an aqueous nutrient solution containing a source of carbon or nitrogen and inorganic salts until the nutrient solution displays antibiotic action against a suitable test organism such as *Candida albicans* and thereafter isolating the active agent.

Suitable nutrient media are described fully in the aforementioned patent.

The cultivation is carried out aerobically, preferably while being agitated or stirred with air or oxygen at a temperature between about 18° and 40° C. for about two to five days. Preferably, the cultivation is carried out in several steps with the preparation first of a seed medium and then inoculating the production medium with the growth from the seed medium. The seed medium may be prepared by inoculating a liquid nutrient medium with a spored mycelium obtained by an approximately 14 day growth on a solid culture medium and allowing it to develop.

After cultivation, the antibiotic may be extracted from the unfiltered culture broth with a substantially water-immiscible organic solvent such as ethyl acetate to recover the antibiotic compound from both the mycelium and the culture broth. Alternatively, the mycelium may be filtered off and the mycelium and the culture filtrate also may be separately extracted.

The solvents then are vaporized off of the extracts to obtain a residue which may be purified by first subjecting it to solvent extraction followed by chromatography. Any of the conventional adsorbents may be employed. Silica gel may be used advantageously and the antibiotic compound may be eluted employing chloroform/methanol with gradually increasing concentration of the polar solvent. Most of the active agent is found in the eluates of 5 to 20 percent methanol.

The papulacandins may be separated into the individual active components or may be employed as a mixture. The major active component is Papulacandin B.

In addition, derivatives may be made of the active components and the derivatives employed.

One group of derivatives are hydrogenation products. The hydrogenation products are principally those compounds obtained by catalytic hydrogenation to a complete saturation of the side chain.

Another group of derivatives are esters. The esters are those compounds in which the hydroxyl group of the alcohols are esterified with carboxylic acid or thiocarboxylic acid. The esterifying acids include alkanoic acids, aromatic or araliphatic acids, as described in the aforementioned patent.

A still another group are ethers. The ethers are those compounds in which one or both phenolic groups are etherified with lower alkanols.

The foregoing derivatives may be obtained by conventional procedures and/or as described in U.S. Pat. No. 4,278,665 which has been incorporated herein by reference.

Derivatives in which the aromatic nucleus is modified are the N-acyl derivatives of 11-aminopapulacandins. The N acyl derivatives may be obtained by first preparing 11-amino-papulacandin and thereafter acylating while temporary protecting the free hydroxyl group present in the 12-position employing conventional synthetic organic procedures. The 11-aminopapulacandin may be prepared by treating a papulacandin derivative having a temporary protecting group in the 12-position with an arylselenic acid anhydride such as $C_6H_5$—(S=O)—O—(S=O)—$C_6H_5$ and hexa-lower alkyldisiloxane to obtain a arylselenoimine and then treating the latter with a reducing agent such as hydrogen sulfide. The preparation of these compounds are fully described in U.S. Pat. No. 4,374,129 which is incorporated by reference.

Another compound belonging to the family of papulacandins and believed to be useful is chaetiacandin which is in an open configuration at the point the papulacandins are in a spiroketal form. This compound may be represented by the formula

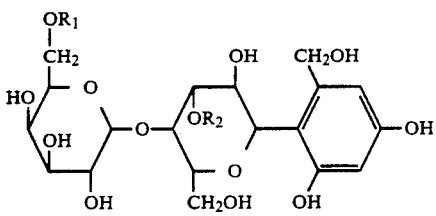

wherein $R_1$ is

and $R_2$ is

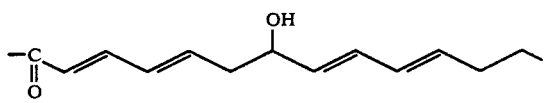

Chaetiacandin may be prepared by the cultivation of *Monochaetia dimorphospora* isolated from soil. The fermentation, isolation and physical properties are described fully in papers by T. Komori et al., J. Antibiotics, XXXVIII (4), 455(1985) and XXXVIII (4 , 544(1985), which citations are incorporated by reference.

Some of the physical properties of chaetiacandin are as follows:

Molecular formula $C_{43}H_{60}O_{16}$.
m.p. 128°~132° C. (dec.).
Optical rotation
$[\alpha]_D^{22}$ $-1.5\pm1°$(C 1, MeOH).
U.V. spectrum (in methanol)

$\lambda_{max}$ 225 nm ($\epsilon$ 32,610)
230 sh ($\epsilon$ 32,500)
263 nm ($\epsilon$ 39,520)

The IR, 'H NMR and $^{13}$CNMR data may be found detailed along with the spectra in the aforecited reference.

These compounds then may be used in the process of the present invention.

The process of the present invention comprises administering to subjects infected with or immune-compromised subjects susceptible to becoming infected with *Pneumocystis carinii*, a therapeutically effective or anti-infective amount of a papulacandin compound.

The efficacy of papulacandin compound for therapeutic and anti-infective purposes in immune-compromised patients may be determined in studies on immunosuppressed rats.

A study suitable for determining probable efficacy of the papulacandin compound for therapeutic and anti-infective purposes in immune-compromised patients may be carried out in the following manner: A suitable number (preferably thirty or multiples thereof) of male Sprague Dawley rats weighing about 300 grams each are immunosuppressed by the addition of dexamethasone to the drinking water (2.0 ml/liter) for six weeks to induce the development of *P. carinii* infections. To enhance the infection, the rats are also maintained on a low protein diet. At the beginning of the seventh week, the rats are divided into three groups of ten rats each. All three groups continue to receive dexamethasone in the drinking water and low protein diet throughout the remainder of the study. The rats in Group I are kept as untreated infected controls, those in Group II are injected intraperitoneally twice daily for two weeks with 0.5 ml of sterile $dH_2O$ containing 2 mg of a selected papulacandin compound, and those in Group III are treated with trimethoprim sulfamethoxazole (TMP SMZ) in the drinking water (208 mg TMP and 1.040 of SMZ/liter) for two weeks, a known treatment for *P. carinii* infections.

At the end of the two week treatment period (a total of eight weeks of immunosuppression), the animals are sacrificed and the lung tissue removed. The lungs from each animal are weighed, and then processed to determine the number of cysts and parasite nuclei for each animal.

Animals treated with a compound having efficacy against *P. carinii* infections would show absence of cysts in the lungs and major reduction in the number of parasite nuclei. Those compounds most effective would show results superior to those seen in animals treated with TMP-SMZ.

From the test results and from the known dosage ranges for TMP-SMZ as applied to man, the dosage range for the papulacandin compound may be determined. A useful range is from about 1.0 to 20.0 mg/kg of body weight.

The outstanding properties are most effectively utilized when the compound is formulated into pharmaceutical compositions with a pharmaceutically acceptable carrier according to conventional pharmaceutical compounding techniques.

The compositions contain at least 1 percent by weight of the active compound. In preparing the compositions, the selected papulacandin compound is intimately admixed with any of the usual pharmaceutically acceptable carriers.

The compositions are preferably prepared in oral dosage form. For liquid preparations, the anti-pneumocystis agent is formulated with liquid carriers such as water, glycols, oil, alcohols, and the like, and for solid preparations such as capsules and tablets, with solid carriers such as starches, sugars, kaolin, ethyl cellulose, calcium and sodium carbonate, calcium phosphate, kaolin, talc, and lactose, and also generally with lubricant such as calcium stearate, together with binders, disintegrating agents and the like. Because of their ease in administration, tablets and capsules represent the most advantageous oral dosage form. It is especially advantageous to formulate the compositions in unit dosage form for ease of administration and uniformity of dosage. Composition in unit dosage form constitutes an aspect of the present invention.

The anti-pneumocystis papulacandin compound may be formulated into compositions for injection and may be presented in unit dosage form in ampoules or in multidose containers, if necessary with an added preservative. The compositions may also take such forms as suspensions, solutions or emulsions in oily or aqueous vehicles such as 0.85 percent sodium chloride or 5 percent dextrose in water, and may contain formulating agents such as suspending, stabilizing and/or dispersing agents. Buffering agents as well as additives such as saline or glucose may be added to make the solutions isotonic. Alternatively, the active ingredients may be in powder form for reconstituting with a suitable vehicle prior to administration.

The term "unit dosage form" as used in the specification and claims refer to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 100 to 1500 milligrams of the papulacandin compound.

The following examples illustrate novel compositions useful in the practice of the present invention but are not to be construed as limiting.

EXAMPLE A 1000 compressed tablets each containing 500 milligrams of Compound IA are prepared from the following formulation:

|  | Grams |
| --- | --- |
| Compound IA | 500 |
| Starch | 750 |
| Dibasic calcium phosphate hydrous | 5000 |
| Calcium stearate | 2.5 |

The finely powdered ingredients are mixed well and granulated with 10 percent starch paste. The granulation is dried and compressed into tablets.

EXAMPLE B 1000 hard gelatin capsules, each containing 210 milligrams of Compound IA are prepared from the following formulation:

| Compound | Grams |
| --- | --- |
| Compound IA | 500 |
| Starch | 250 |
| Lactose | 750 |
| Talc | 250 |
| Calcium stearate | 10 |

A uniform mixture of the ingredients if prepared by blending and used to fill two-piece hard gelatin capsules.

EXAMPLE C 250 milliliters of an injectable solution are prepared by conventional procedures having the following formulation:

| Dextrose | 12.5 grams |
| --- | --- |
| Water | 250 milliliters |
| Compound IB | 400 milligrams |

The ingredients are blended and thereafter sterilized for use.

EXAMPLE D 1000 compressed tablets each containing 500 milligrams of Compound IB are prepared from the following formulation in a manner of Example A.

|  | Grams |
| --- | --- |
| Compound IB | 500 |
| Starch | 750 |
| Dibasic calcium phosphate hydrous | 5000 |
| Calcium stearate | 2.5 |

EXAMPLE E 1000 gelatin capsules each containing 176 milligrams of Compound IB may be prepared by blending the following formulation and used to fill capsules.

|  | Grams |
| --- | --- |
| Compound IB | 500 |
| Starch | 250 |
| Lactose | 750 |
| Talc | 250 |
| Calcium stearate | 10 |

What is claimed is:

1. A method for treating *Pneumocystis carinii* infection in a mammalian host which comprises administering to said host an anti-infective amount of a compound represented by the formula

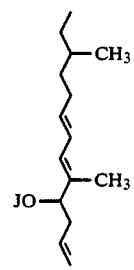

13
-continued

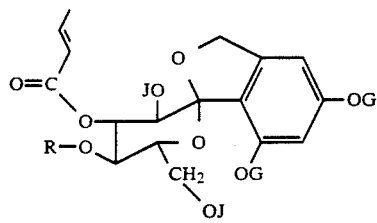

wherein R is (A)

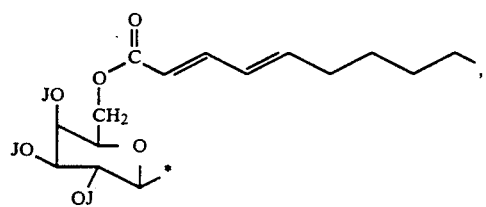

(B)

14
-continued

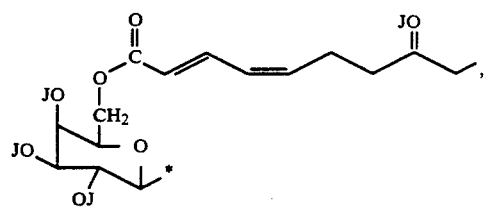

(D)  H—  (ID)

wherein:
* is the point of bonding
G is hydrogen or lower alkyl; and
J is hydrogen or acyl containing from 1 to 20 carbon atoms provided that at least one of J and G is hydrogen.

2. A method for treating *Pneumocystis carinii* infections in a mammalian host which comprises administering to said host an anti-infective amount of a papulacandin compound which is a papulacandin antibiotic selected from the group consisting of:

(A) Papulacandin A having the formula

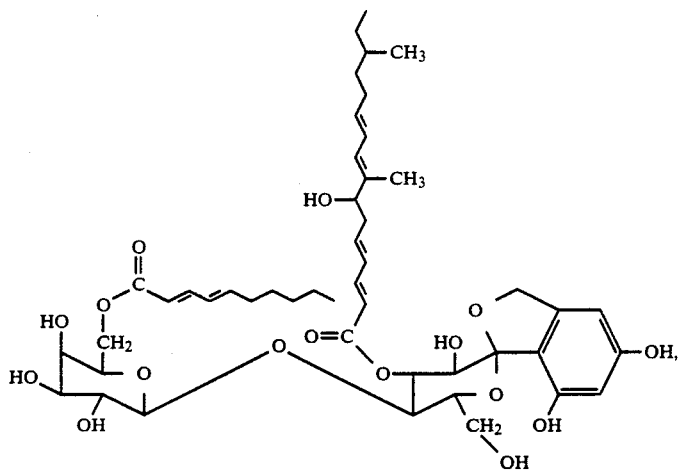

(B) Papulacandin B having the formula

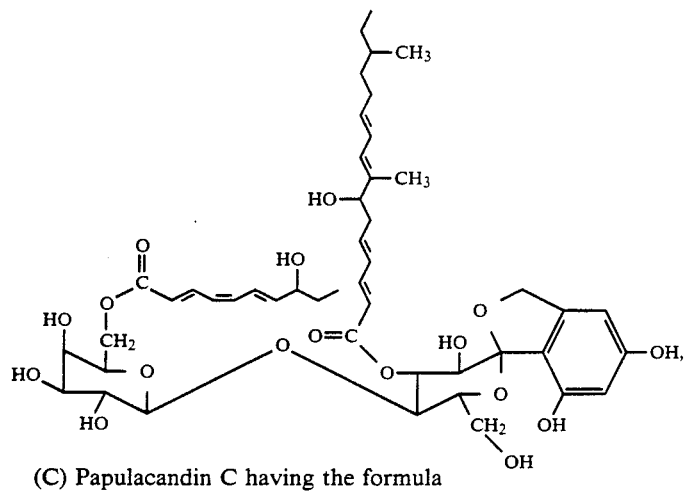

(C) Papulacandin C having the formula

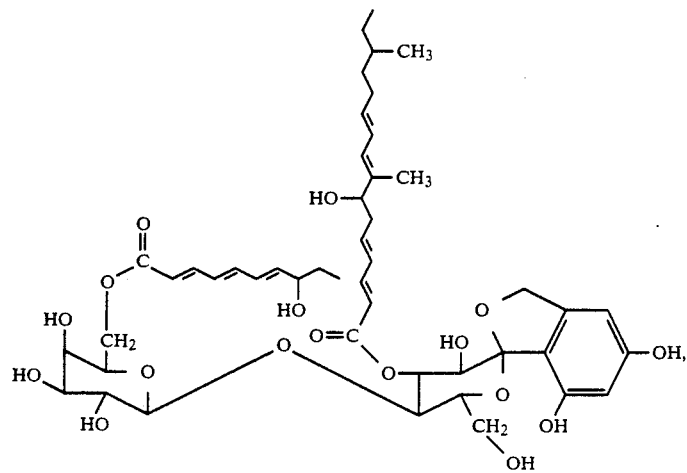

(D) Papulacandin D having the formula

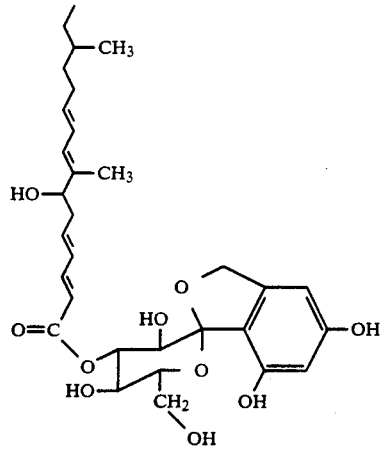

(E) Papulacandin E and mixtures thereof.

3. A method according to claim 1 wherein the active agent is administered to a mammalian host with an impaired immune system and infected with *Pneumocystis carinii*.

4. A method according to claim 1 wherein the active agent is administered to a mammalian host with AIDS and infected with *Pneumocystis carinii*.

5. A method according to claim 1 wherein the active agent is administered at a dose of from about 1.0 to 20.0 mg/kg of body weight.

* * * * *